(12) United States Patent
Bhardwaj et al.

(10) Patent No.: US 8,435,975 B2
(45) Date of Patent: May 7, 2013

(54) STEROIDAL ESTERS OF 17-OXIMINO-5-ANDROSTEN-3BETA-OL

(75) Inventors: Tilak Raj Bhardwaj, Chandigargh (IN); Manoj Kumar, Chandigargh (IN); Neelima Dhingra, Chandigarh (IN); Neraj Mehta, Chandigarh (IN)

(73) Assignee: Council of Scientific & Industrial Research, New Delhi (IN)

( * ) Notice: Subject to any disclaimer, the term of this patent is extended or adjusted under 35 U.S.C. 154(b) by 170 days.

(21) Appl. No.: 12/733,415

(22) PCT Filed: Aug. 14, 2008

(86) PCT No.: PCT/IN2008/000513
§ 371 (c)(1),
(2), (4) Date: Jul. 8, 2010

(87) PCT Pub. No.: WO2009/027994
PCT Pub. Date: Mar. 5, 2009

(65) Prior Publication Data
US 2010/0292201 A1 Nov. 18, 2010

(30) Foreign Application Priority Data
Aug. 24, 2007 (IN) .......................... 1805/DEL/2007

(51) Int. Cl.
*A61K 31/568* (2006.01)
*C07J 41/00* (2006.01)
*A61P 5/28* (2006.01)

(52) U.S. Cl.
USPC ........................................ 514/182; 552/519

(58) Field of Classification Search .................. 514/182; 552/519
See application file for complete search history.

(56) References Cited

PUBLICATIONS

Brueckner et al. ( abstract of DE 1159941).Document No. 60:52932, Accession No. 1964:52932, Title: 17-Oximino-3-oxoandrostanes).*
Matkovics et al. (Magyar Kemiai Folyoirat (1966), 72(7), 303-7Accession No. 1966:465704, HCAPLUS, Document No. 65:65704 Original Reference No. 65:12252c-f).*
Krstic et al. (Steroids. May 2007;72(5):406-14. Epub Mar. 13, 2007).*
Liao; "Cellular Receptors and Mechanisms of Action of Steroid Hormones"; The Ben May Laboratory for Cancer Research and the Department of Biochemistry, The University of Chicago, Chicago, Illinois; 1975.
Levy et al.; Epristeride is a Selective and Specific Uncompetitive Inhibitor of Human Steroid 5α-Reductase Isoform 2; Steroid. Biochem. Molec. Biol.; vol. 48, No. 2/3; 1994.
Foley et al.; "An Update on the Use of 5α-Reductase Inhibitors"; Drugs of Today; vol. 40, No. 3, 2004.
Culig et al.; "Regulation of Prostatic Growth and Function by Peptide Growth Factors"; The Prostate 28: 392-405 (1996).
Reid et al.; "Antiandrogens in Prostate Cancer"; Investigational New Drugs 17; 1999.
Berry et al.; "The Development of Human Benign Prostatic Hyperplasia With Age"; The Journal of Urology; 1984.

* cited by examiner

*Primary Examiner* — Sabiha N Qazi
(74) *Attorney, Agent, or Firm* — Abelman, Frayne & Schwab

(57) ABSTRACT

The present invention relates to steroidal esters of 17-oximino-5-androsten-3-ol, of compound of general formula (A) wherein R is selected from a group consisting of arylalkyl, aryl, substituted aryl. The ester derivatives are synthesized starting from Dehydroandrosterone acetate. The compounds were tested for their antiproliferative activity and 5α-reductase inhibitory activity in comparison to Finasteride. Decreased androgen level have been found in serum of animal treated with newly synthesized compounds. These compounds have also shown better cytotoxicity in comparison to reference drug Finasteride. Thus such compounds can be useful in treatment of androgen dependent disorder of prostate alone or by synergistic effect they can decrease the size of prostate due to their antiproliferative activity.

8 Claims, 4 Drawing Sheets

STEROIDAL ESTERS OF 17-OXIMINO-5-ANDROSTEN-3BETA-OL

FIELD OF THE INVENTION

The present invention relates to novel steroidal esters of 17-oximino-5-androsten-3βol. The present invention particularly relates to steroidal esters of compound of formula A wherein R is selected form a group consisting of alkyl, aryl, substituted aryl.

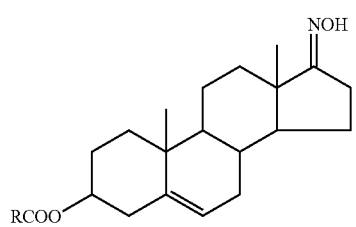

Formula A

The compounds are useful as 5α-reductase inhibitor and androgen dependent disorders for the treatment of benign prostatic hyperplasia.

BACKGROUND OF THE INVENTION

Hyperplasia is a general medical term referring to excess cell proliferation and benign prostatic hyperplasia is non-malignant enlargement of the prostate gland caused by increase in the number of stromal and epithelial cells resulting in obstruction of the proximal urethra, thus causes urinary flow disturbances [Roehrborn, C. G. *BJU Int.* 2006, 97, 7; Emberton, M. *BJU Int.* 2006, 97, 12 and Fitzpatrick, J. M. *BJU Int.* 2006, 97, 3]. It is leading disorder of the elderly male population and prevalence increases with age affecting around 80% by the age of 80 years. Nearly all men will develop microscopic BPH (Benign Prostatic Hyperplasia) by the age of 90 [Berry, S. J. et. al., *Br. J. Urol.*, 1995, 5, 85].

Number of different causes for the overgrowth includes age, late activation of cell growth, abnormal increase in the clonal expansion of transit cell and change in ratios of androgen-estrogen level, which promote growth of prostatic tissue [Theomher, M. et al. *Prostate*, 1996, 28, 392 and Jenkins, E. P et al. *J. Clin. Invest.*, 1992, 89, 293]. But the most widely accepted hypothesis is the dihydrotestosterone hypothesis which postulates that BPH occurs following an age related changes in the prostate androgen metabolism which favours accumulation of dihydrotestosterone.

Dihydrotestosterone (DHT), the most potent circulating androgen hormone, is produced by NADPH dependent stereoselective reduction of testosterone (T), under catalysis of the enzyme steroid 5α-reductase (5AR) as shown in FIG. 1 and FIG. 2 [Hitoshi, T. et al. *Chem. Pharm. Bull.*, 2000, 48, 552]. Within prostate dihydrotestosterone binds to cytosol androgen receptor protein (AR) and DHT-AR complex enters the nucleus, interacts with DNA binding sites where it stimulates the RNA synthesis (FIG. 1) [Liao, S. *Int. Rev. Cytol.* 1975, 41, 87]. The concentration of dihydrotestosterone is 2.5 fold higher than in normal prostate.

Therefore, inhibition of androgen action by 5α-reductase is a logical treatment of 5α-reductase activity disorder i.e. benign prostatic hyperplasia.

Androgen suppression causes reduction in prostatic volume which is believed to decrease the static component of bladder outlet obstruction resulting from benign prostatic hyperplasia (FIG. 2) [Reid, P. et al. *J. Clin Invest. New Drugs.* 1999, 17, 271]. With the discovery of two 5α-reductase isozymes, their physiological and pharmacological roles in BPH, a significant research has been carried out to synthesize and evaluate nonsteroidal [Marisa, C. et al. *Chem. Pharm. Bull.*, 2001, 49, 525, Frye, *J. Med. Chem.*, 1994, 37, 2352] and steroidal compounds [Leny, M. A. et al. *J. Steroid Biochem. Mol. Biol.*, 1994, 48, 197, Toshiaki, K. et al., *Chem. Pharm. Bull.*, 1996, 44, 115] as competitive [4-azasteroids, 6-azasteroids] or non-competitive [3-carboxysteroids] inhibitors of 5α-reductase. Of these, only Finasteride (3) (MK-906) [Foley, C. L. et al. *Drugs of Today* 2004, 40, 213], and Dutasteride (4) [Susumu, T.; et al. *Chem. Pharm. Bull.*, 2000, 48, 1689] are being used clinically in the treatment of benign prostatic hyperplasia.

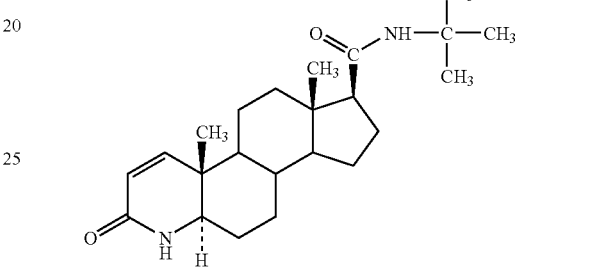

(3)

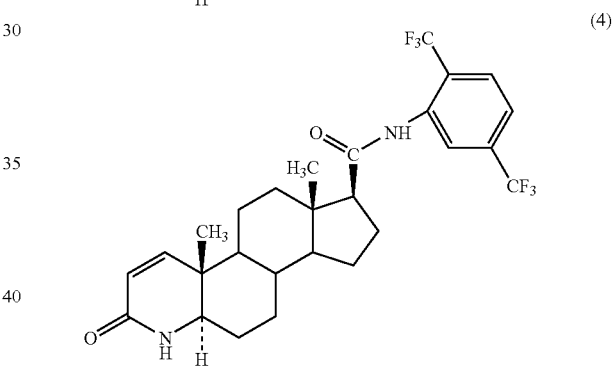

(4)

It has been reported that various steroidal compounds possess high affinity for 5α-reductase inhibitors on account of their ability to form a coordinate bond with iron heame [Hartmann, R. W. et al.; J. *J. Med. Chem.* 2000, 43, 4266]. On other hand, progesterone esters (5,6) synthesised by Mexico laboratory exhibited high antiandrogenic activity [Cabeza, M. et al.; *Chem. Pharm. Bull.* (*Tokyo*) 1999, 47, 1232 and Cabeza, M. et al. *Chem. Pharm. Bull.* (*Tokyo*) 2001, 49, 1081.

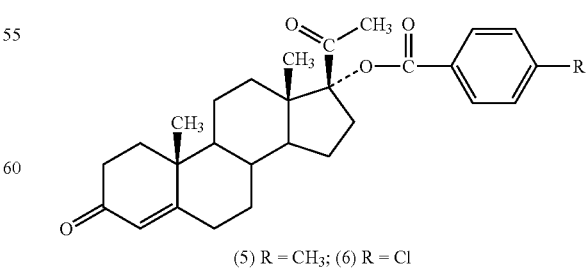

(5) R = CH$_3$; (6) R = Cl

On long term usage of Finasteride and Dutasteride the most common reported side effect include decreased libido, decreased ejaculate amount and erectile dysfunction. Whereas progesterone esters have been found to possess good antiandrogenic activity but are still under clinical investigation.

Based on these observations, it was envisaged to synthesize 17-oximino-5-androsten-3β-yl esters (10-16). Benign prostatic hyperplasia is also described by abnormal increase in the number of cells in prostate which may result not only from increased cell proliferation but also from decreased level in programmed cell death (apoptosis). These analogues were evaluated for 5α-reductase inhibitory activity and antiproliferative activity. These compounds may be useful in androgen dependent benign prostatic hyperplasia, by acting not only at the molecular level for the underlying cause of the disease but also decreasing the growth of prostate by killing cells.

OBJECTS OF THE INVENTION

The main object of the present invention is to provide novel steroidal esters of 17-oximino-5-androstene-3β-ol.

Another object of the invention is to provide a process for preparation of novel steroidal esters of 17-oximino-5-androstene-3β-ol.

One more object of the present invention is to provide the compounds useful for the treatment of benign prostatic hyperplasia.

Still another object of the invention is to provide the compounds having antiproliferative activity with a >90% growth inhibition of DU-145 cell.

SUMMARY OF THE INVENTION

The present invention relates to steroidal esters derivative of 17-oximino-5-androsten-3-ol. The compounds have been synthesized starting from Dehydroandrosterone acetate. Newly synthesized compounds were tested for their antiproliferative activity and 5α-reductase inhibitory activity in comparison to Finasteride. Decreased androgen level has been found in serum of animal treated with newly synthesized compounds. These compounds have also shown better cytotoxicity in comparison to reference drug Finasteride. Thus such compounds can be useful in treatment of androgen dependent disorder of prostate alone or by synergistic effect they can decrease the size of prostate due to their antiproliferative activity.

DETAILED DESCRIPTION OF THE INVENTION

Figure 1:
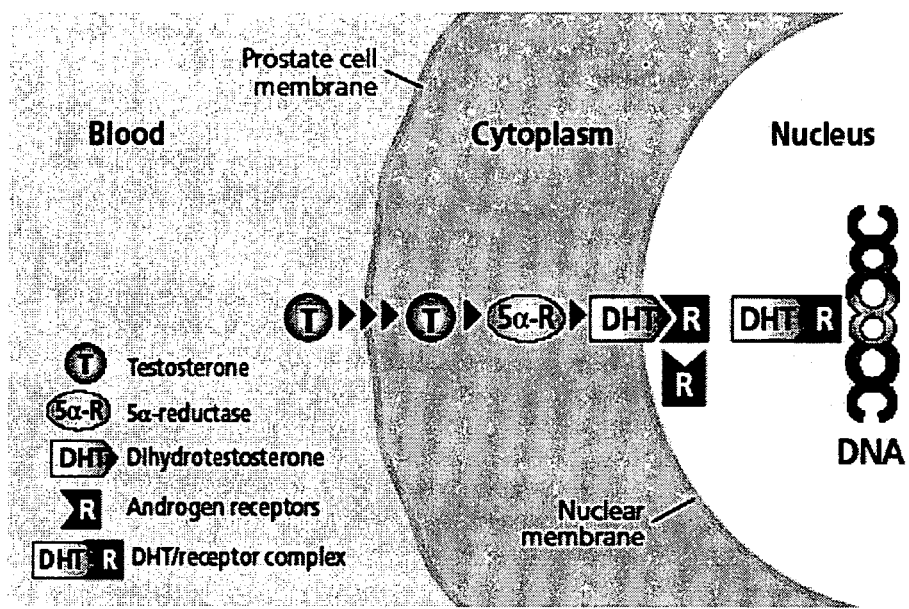
FIG. 1 shows the production of Dihydrotestosterone from Testosterone in-situ.
Figure 2:
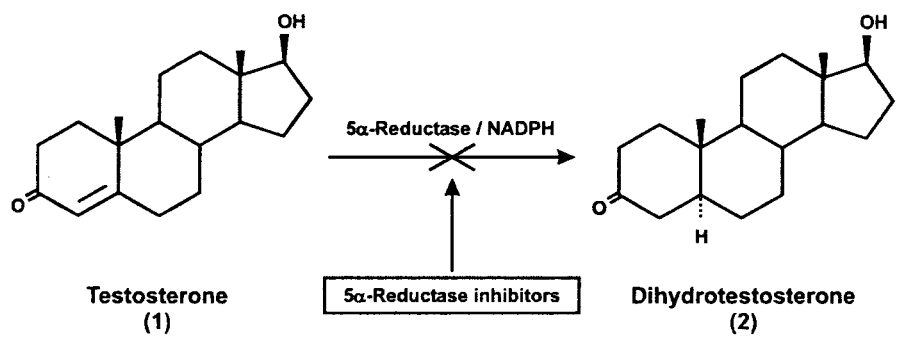
FIG. 2 shows the chemical reaction involved in the production of Dihydrotestosterone from Testosterone.

Accordingly the present invention provides a compound of general formula A, pharmaceutically acceptable salt thereof;

General formula A wherein R is selected form a group consisting of arylalkyl, aryl, substituted aryl.

In an embodiment of the invention wherein the aryalkyl group may be selected from a group consisting of benzyl, phenoxymethyl, or substituted arylalkyl such as 4-chlorobenzyl, 4-nitrobenzyl, 4-methylbenzyl, 4-aminobenzyl, 4-chlorophenoxymethyl, 4-nitrophenoxymethyl, 4-methylphenoxymethyl, 4-aminophenoxymethyl.

In another embodiment of the invention wherein the aryl group may be selected form a group consisting of (i) 4-chlorophenyl (10); (ii) 4-nitrophenyl (11); (iii) 4-methylphenyl (p-tolyl) (12); (iv) phenyl (13); (v) 4-aminophenyl (14); (vi) 4-hydroxyphenyl (15); (vii) phenoxymethyl (16)

In yet another embodiment of the invention wherein the pharmaceutically acceptable salt may be selected form a group consisting of hydrochloride, sulphates, phosphates acetates, propionates; and sodium, potassium and calcium salts of the phenolic hydroxyl groups containing substrates.

In still another embodiment of the invention wherein the representative compounds of formula A comprising;
(i) 17-oximino-5-androsten-3β-yl 4-chlorobenzoate (10)
(ii) 17-oximino-5-androsten-3β-yl 4-nitrobenzoate (11)
(iii) 17-oximino-5-androsten-3β-yl 4-methylbenzoate (12)
(iv) 17-oximino-5-androsten-3β-yl benzoate (13)
(v) 17-oximino-5-androsten-3β-yl 4-aminobenzoate (14)
(vi) 17-oximino-5-androsten-3β-yl 4-hydroxybenzoate (15)
(vii) 17-oximino-5-androsten-3β-yl phenoxyacetate (16)

In a further embodiment of the invention wherein the compounds are useful as 5α-reductase inhibitor, androgen dependent disorders.

In another embodiment of the invention wherein the compounds showed antiproliferative activity with a >90% growth inhibition of DU-145 cell at a concentration of 5.0 μg/ml.

In another embodiment of the invention wherein the compounds showed increase of serum level of testosterone in rats as compared to control at a dose of 40 mg/kg.

In another embodiment of the invention wherein the compounds are having LC50 in the range of 19.5 to 89.4 μm.

In another embodiment of the invention wherein the compounds are non-toxic at a concentration ranging between 0.01 μg/ml to 5.0 μg/ml.

Accordingly, the present invention provides a process for preparation of novel steroidal esters of 17-oximino-5-androstene-3β-ol of formula A, wherein the process steps comprising:

(i) reacting 17-oximino-5-androsten-3β-ol with an organic acid and dicyclohexylcarbodiimide (DCC) in anhydrous dichloromethane for a period ranging between 24-48 hrs at a temperature ranging between 20 to 25° C.

(ii) filtering the precipitated dicyclohexylurea (dcu) and removing the solvent from the filtrate under vacuum and the residue was crystallized to obtain the desired product.

Accordingly, the present invention provides a pharmaceutical composition comprising: a therapeutically effective amount of a compound of formula A or a pharmaceutically acceptable salt thereof optionally along with a pharmaceutically acceptable carrier, percipient, diluent.

Figure 3:
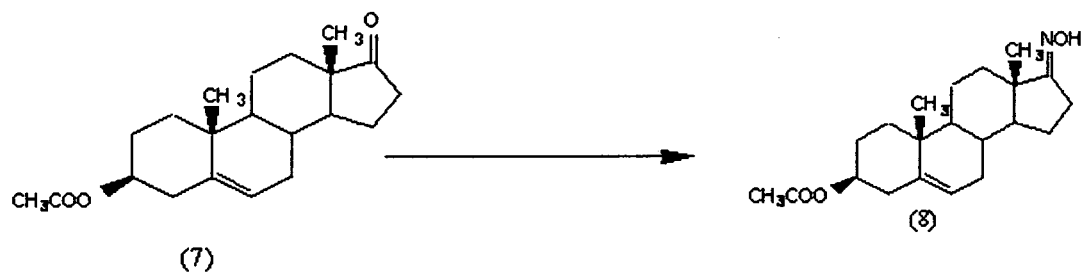
FIG. 3 shows the conversion of 17-Oxo-5-androsten-3β-yl acetate (7) to its oxime (8) by refluxing in ethanol with hydroxylamine hydrochloride and sodium acetate.

In the proposed research project novel steroidal esters of 17-oximino 5-androsten-3β-ol were synthesized in two steps, starting from dehydroepiandrosterone acetate, which was prepared from the diosgenin [Marker, R. E. et al.; *J. Amer. Chem. Soc.* 1939, 61, March, J. *Advanced Organic Chemistry*; John Wiley and Sons: New York, 2001, p 395. and Lemeiux, U. et al. *Can. J. Chem.* 1955, 33, 1701]. The oxime moiety at C-17 of the steroid nucleus was incorporated as proposed in FIG. 3. 17-Oxo-5-androsten-3β-yl acetate (7) was converted to its oxime (8) by refluxing in ethanol with hydroxylamine hydrochloride and sodium acetate. In infrared spectrum stretching due to NOH, C=O (ester) and C—O (ester) were found at 3400, 1740 and 1245 cm$^{-1}$, respectively. In NMR spectrum signals were recorded at δ 2.3 (s, 3H, CH$_3$COO), 4.60 (m, 1H, 3α-H), 5.4 (br, 1H, 6-vinylic) and 8.43 ppm (1H, NOH).

Figure 4:
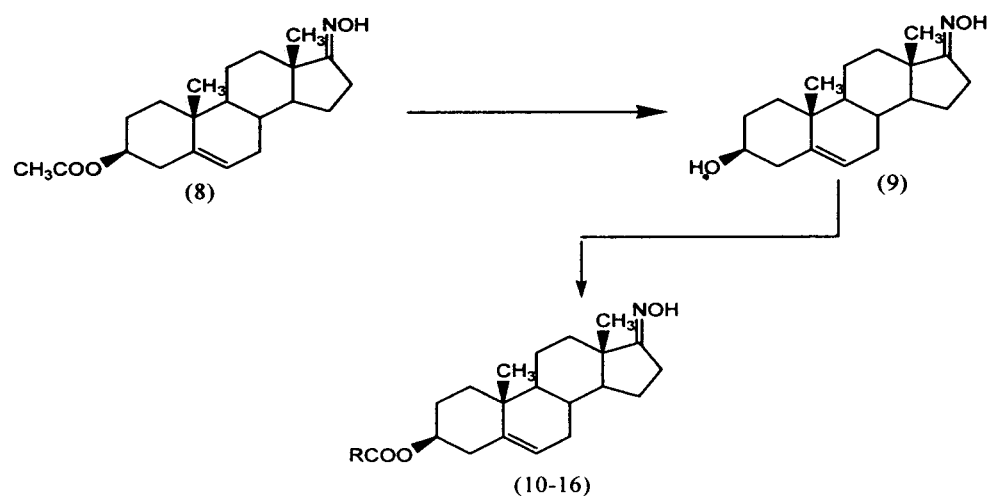
FIG. 4 shows the esterification and hydrolysis of the oxime (8) 17-Oximino-5-androsten-3β-yl acetate (8) was hydrolyzed with methanolic potassium hydroxide to get 17-Oximino-5-androsten-3β-ol acetate (9). Products are as shown 10-16 are the final products obtain reacting with corresponding acids as illustrated in examples 1-7.

The oxime 8 was hydrolysed and esterified as given in FIG. 4.

17-Oximino-5-androsten-3β-yl acetate (8) was hydrolyzed with methanolic potassium hydroxide to get 17-oximino-5-androsten-3β-ol (9). In $^1$H-NMR spectrum signals for 3α and 6-vinylic protons appeared at δ 4.54 and δ 5.22, respectively. IR spectrum showed disappearance of the stretching due to acetate carbonyl at 1740 cm$^{-1}$. 17-Oximino-5-androsten-3β-ol (9) was reacted with respective acid and dicyclohexylcarbodiimide (DCC) in anhydrous dichloromethane. The reaction mixture was stirred for 48 hr at room temperature and completion of the reaction was monitored by TLC. The precipitated dicyclohexylurea (DCU) was filtered, solvent removed under vacuum and the residue was crystallized from ethyl acetate:petroleum ether (60:80) to obtain the desired product.

Following examples are given by way of illustration and should not construed to limit the scope of the invention.

EXAMPLE 1

17-OXIMINO-5-ANDROSTEN-3β-YL 4-CHLOROBENZOATE (10)

To the stirred solution of 17-oximino-5-androsten-3β-ol (9) (0.5 g, 1.6 mmol) and dicyclohexylcarbodiimide (DCC) (0.34 g, 1.6 mmol) in anhydrous dichloromethane (30.0 ml), 4-chlorobenzoic acid (0.26 g, 1.6 mmol) was added. The reaction mixture was stirred for 48 hr at room temperature (20-25°) and completion of the reaction was monitored by TLC. The precipitated dicyclohexylurea (DCU) was filtered and the solvent removed under vacuum. The resulting residue was crystallized from ethyl acetate:petroleum ether (60:80) to give 17-oximino-5-androsten-3β-yl 4-chlorobenzoate (10) (0.30 g, 60.0%) mp 167-170° C.

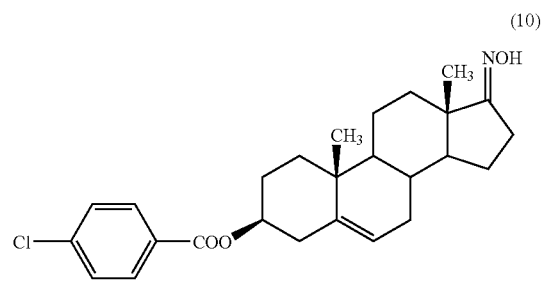

(10)

Anal.:
mp 167-170° C.
IR (KBr): 3310, 2930, 1740, 1650 and 1235 cm$^{-1}$
$^1$H-NMR (CDCl$_3$): δ 1.03 (s, 3H, 18-CH$_3$), 1.04 (s, 3H 19-CH$_3$), 2.17 (1H, NOH), 4.15 (m, 1H, 3α-H), 5.40 (br, 1H, 6-vinylic), 7.50 (d, 2H, 3-CH and 5-CH aromatic) and 7.97 ppm (d, 2H, 2-CH and 6-CH aromatic)
Calcd for C$_{26}$H$_{32}$NO$_3$Cl: N, 3.17. Found: N, 3.25.

EXAMPLE 2

17-OXIMINO-5-ANDROSTEN-3β-YL 4-NITROBENZOATE (11)

To the stirred solution of 17-oximino-5-androsten-3β-ol (9) (0.5 g, 1.6 mmol) and dicyclohexylcarbodiimide (DCC) (0.34 g, 1.6 mmol) in anhydrous dichloromethane (30.0 ml), p-nitrobenzoic acid (0.27 g, 1.6 mmol) was added. The reaction mixture was stirred for 48 hr at room temperature (20-25°) and completion of the reaction was monitored by TLC. The precipitated dicyclohexylurea (DCU) was filtered and the solvent removed under vacuum. The resulting residue was crystallized from ethyl acetate:petroleum ether (60:80) to give 17-oximino-5-androsten-3β-yl 4-nitrobenzoate (11) (0.34 g, 68.0%) mp 185-188° C.

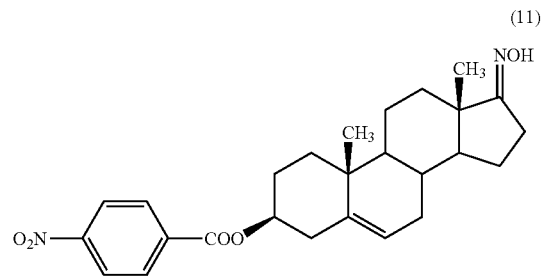

(11)

Anal.:
mp 185-188° C.
IR (KBr): 3300, 2930, 1700, 1650 and 1234 cm$^{-1}$
$^1$H-NMR (CDCl$_3$): δ 0.89 (s, 3H, 18-CH$_3$), 1.03 (s, 3H 19-CH$_3$), 3.85 (m, 1H, 3α-H), 5.4 (br, 1H, 6-vinylic), 6.65 (d, 2H, 3-CH and 5-CH aromatic), 7.87 (d, 2H, 2-CH and 6-CH aromatic)
Calcd for C$_{26}$H$_{32}$N$_2$O$_5$: N, 6.19. Found: N, 5.64.

EXAMPLE 3

17-OXIMINO-5-ANDROSTEN-3β-YL 4-METHYLBENZOATE (12)

4-Methylbenzoic acid (p-toluic acid) (0.22 g, 1.6 mmol) (0.16 g, 1.6 mmol) was added to the stirred solution of 17-oximino-5-androsten-3β-ol (9) (0.5 g, 1.6 mmol) and dicyclohexylcarbodiimide (DCC) (0.34 g, 1.6 mmol) in anhydrous dichloromethane (30.0 ml). The reaction mixture was stirred for 48 hr at room temperature (20-25°) and completion of the reaction was monitored by TLC. The precipitated dicyclohexylurea (DCU) was filtered, solvent removed under vacuum and the residue was crystallized from ethyl acetate:petroleum ether (60:80) to obtain 12 (0.29 g, 58.0%) mp 135-139° C.

(12)

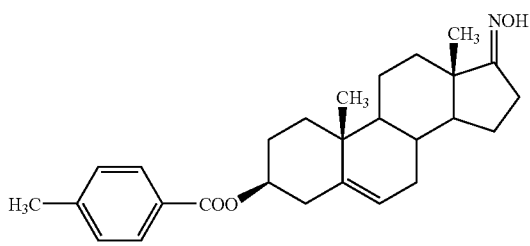

Anal.:
mp 135-139° C.
IR (KBr): 3310, 2930, 1700, 1650 and 1235 cm$^{-1}$
$^1$H-NMR (CDCl$_3$): δ 0.89 (s, 3H, 18-CH$_3$), 1.03 (s, 3H 19-CH$_3$), 2.41 (1H, NOH), 4.08 (m, 1H, 3α-H), 6.25 (br, 1H, 6-vinylic), 7.20 (d, 2H, 3-CH and 5-CH aromatic) and 7.43 ppm (d, 2H, 2-CH and 6-CH aromatic)
Calcd for C$_{27}$H$_{35}$NO$_3$: N, 3.32. Found: N, 3.77.

EXAMPLE 4

17-OXIMINO-5-ANDROSTEN-3β-YL BENZOATE (13)

17-Oximino-5-androsten-3β-ol (9) (0.5 g, 1.6 mmol) and dicyclohexylcarbodiimide (DCC) (0.34 g, 1.6 mmol) was dissolved in anhydrous dichloromethane (30.0 ml) and stirred. To this was added benzoic acid (0.2 g, 1.6 mmol). The reaction mixture was stirred for 48 hr at room temperature (20-25°) and completion of the reaction was monitored by TLC. The precipitated material was filtered, solvent removed under reduced pressure to give residue which was crystallized from ethyl acetate:petroleum ether (60:80) to get 17-oximino-5-androsten-3β-yl benzoate (13) (0.32 g, 64.0%) mp 165-170° C.

(13)

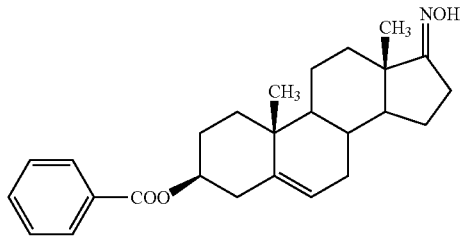

Anal.:
mp 165-170° C.
IR (KBr): 3300, 2930, 1700, 1650 and 1235 cm$^{-1}$
$^1$H-NMR (CDCl$_3$): δ 0.89 (s, 3H, 18-CH$_3$), 1.1 (s, 3H 19-CH$_3$), 4.07 (m, 1H, 3α-H), 5.40 (br, 1H, 6-vinylic) and 6.84-7.28 (m, 5H, aromatic)
Calcd for C$_{26}$H$_{33}$NO$_3$: N, 3.44. Found: N, 3.74.

EXAMPLE 5

17-OXIMINO-5-ANDROSTEN-3β-YL 4-AMINOBENZOATE (14)

p-Aminobenzoic acid (0.22 g, 1.6 mmol) was added to the stirred solution of 17-oximino-5-androsten-3β-ol (9) (0.5 g, 1.6 mmol) and dicyclohexylcarbodiimide (DCC) (0.34 g, 1.6 mmol) in anhydrous dichloromethane (30.0 ml). The reaction mixture was stirred for 48 hr at room temperature (20-25°) and completion of the reaction was monitored by TLC. The precipitated dicyclohexylurea (DCU) was filtered, solvent removed under vacuum and the residue was crystallized from ethyl acetate:petroleum ether (60:80) to obtain 17-oximino-5-androsten-3β-yl 4-aminobenzoate (14) (0.28 g, 56.0%) mp 165-168° C.

(14)

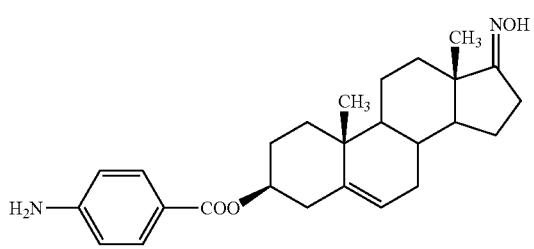

Anal.:
mp 165-168° C.
IR (KBr): 3330, 2930, 1700, 1630 and 1240 cm$^{-1}$
$^1$H-NMR (CDCl$_3$): δ 0.93 (s, 3H, 18-CH$_3$), 1.05 (s, 3H 19-CH$_3$), 2.17 (1H, NOH), 4.08 (m, 1H, 3α-H), 6.20 (br, 1H, 6-vinylic), 7.22 (d, 2H, 3-CH and 5-CH aromatic) and 8.26 ppm (d, 2H, 2-CH and 6-CH aromatic)
Calcd for C$_{26}$H$_{34}$N$_2$O$_3$: N, 6.63. Found: N, 6.79.

EXAMPLE 6

17-OXIMINO-5-ANDROSTEN-3β-YL 4-HYDROXYBENZOATE (15)

17-Oximino-5-androsten-3β-ol (9) (0.5 g, 1.6 mmol) was taken in anhydrous dichloromethane (30.0 ml). Dicyclohexylcarbodiimide (DCC) (0.34 g, 1.6 mmol) was added followed by p-hydroxybenzoic acid (0.23 g, 1.6 mmol). Reaction mixture was stirred at room temperature for 24-48 hr and completion of the reaction was monitored by TLC. The reaction mixture was filtered to remove precipitated dicyclohexylurea (DCU). Excess of solvent was removed under vacuum and the product was crystallized from ethyl acetate:petroleum ether (60:80) to yield 17-oximino-5-androsten-3β-yl 4-hydroxybenzoate (15) (0.31 g, 62.0%) mp 177-182° C.

(15)

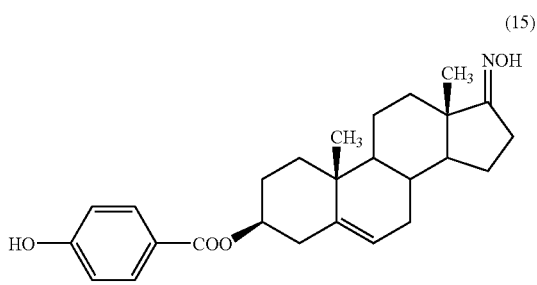

Anal.:
mp 177-182° C.
IR (KBr): 3310, 2930, 1710, 1680 and 1235 cm$^{-1}$
$^1$H-NMR (CDCl$_3$): δ 0.89 (s, 3H, 18-CH$_3$), 1.05 (s, 3H 19-CH$_3$), 2.17 (1H, NOH), 4.18 (m, 1H, 3α-H), 6.35 (br, 1H, 6-vinylic), 6.83 (d, 2H, 3-CH and 5-CH aromatic) and 7.46 ppm (d, 2H, 2-CH and 6-CH aromatic)
Calcd for C$_{26}$H$_{33}$NO$_4$: N, 3.31. Found: N, 3.32.

EXAMPLE 7

17-OXIMINO-5-ANDROSTEN-3β-YL PHENOXYACETATE (16)

To the stirred solution of 17-Oximino-5-androsten-3β-ol (9) (0.5 g, 1.6 mmol) and dicyclohexylcarbodiimide (DCC) (0.342 g, 1.6 mmol) in anhydrous dichloromethane (30.0 ml), phenoxyacetic acid (0.24 g, 1.6 mmol) was added. The reaction mixture was stirred for 48 hr at room temperature (20-25°) and completion of the reaction was monitored by TLC. The precipitated dicyclohexylurea (DCU) was filtered and the solvent removed under vacuum. The resulting residue was crystallized from ethyl acetate:petroleum ether (60:80) to give 17-oximino-5-androsten-3β-yl phenoxyacetate (16) (0.27 g, 54.0%) mp 118-122° C.

(16)

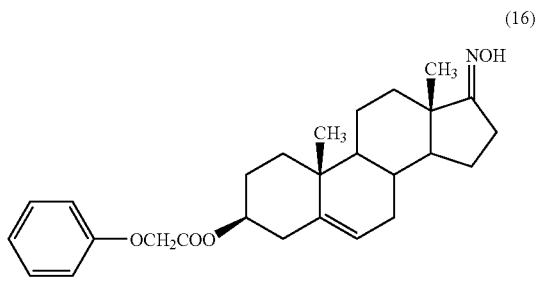

Anal.:
mp 118-122° C.
IR (KBr): 3200, 2940, 1750, 1650 and 1220 cm$^{-1}$
$^1$H-NMR (CDCl$_3$): δ 0.88 (s, 3H, 18-CH$_3$), 1.02 (s, 3H 19-CH$_3$), 4.60 (s, 2H, OCH$_2$), 4.7 (m, 1H, 3α-H), 5.40 (br, 1H, 6-vinylic) and 7.29 (m, 5H, aromatic)
Calcd for C$_{27}$H$_{35}$NO$_4$: N, 3.20. Found: N, 3.60.
Biological Evaluation The synthesized steroidal derivatives have been evaluated for in vitro antiproliferative activity using DU-145 cell lines and in vivo studies i.e. 5α-Reductase Inhibitory activity [George, F. W. et al. *Endocrinology*, 1989, 125, 2434]

1) In Vitro Antiproliferative Activity Against Human Prostate Cancer Cell Line (DU-145)

Compounds were screened for antiproliferative activity on human prostate cell line DU-145 at National Centre of Human Genome Studies and Research. Panjab University, Chandigarh. All the compounds (10 to 16), Finasteride and starting material (9) were tested at five different concentrations: 0.01, 0.5, 1.0, 2.0, and 5.0 µg/ml. Finasteride was the positive control in this growth inhibitory assay.

Growth Inhibitory Activity Assay (MTT Assay)

We investigated the effect of newly synthesized compounds on cell growth inhibition using MTT assay. This assay quantifies the viable cells by observing the reduction of tetrazolium salt, MTT to formazan crystals by the live cells. Based on the absorbance of the cell sample after the test is carried out, cell viable can be measured [Loveland, B. E.; Jones, T. G.; Mackay. I. R.; Vaillant, F.; Wang, Z. X.; Hertzog, P. J. *Biochem. International* 1992, 27, 501 and Wright, S. A.; Thomas, L. N.; Douglas, R. C.; Lazier, C. B.; Rittmaster, R. S. *J. Clin. Invest.* 1996, 98, 2558]. Cells were cultured at a density of 5×10$^3$ cells/well in 96 well plates at 37° C. in 5.0% CO$_2$ atmosphere and were allowed to attach for 24 hr. The cells were treated in triplicate with graded concentration of sample and reference drug Finasteride at 37° C. for 48 hr. A 20 µl aliquot of MTT solution was added directly to all the appropriate wells. Following 4 hr of incubation at 37 µl, the media was removed and formazan crystals, which results from the reduction of MTT by active cell were dissolved in 100 µl DMSO and vigorously mixed to dissolve the reacted dye. The absorbance of each well was read on Elisa plate reader (Merck) at 570 nm. The spectrometer was calibrated to zero absorbance using culture medium without cells. The relative cell viability (%) related to control well containing cell culture medium without drug was calculated by [A]test/[A]control×100.

% Growth Inhibition=$[OD]_{control}-[OD]_{test}/[OD]_{control} \times 100$

Figure 5:
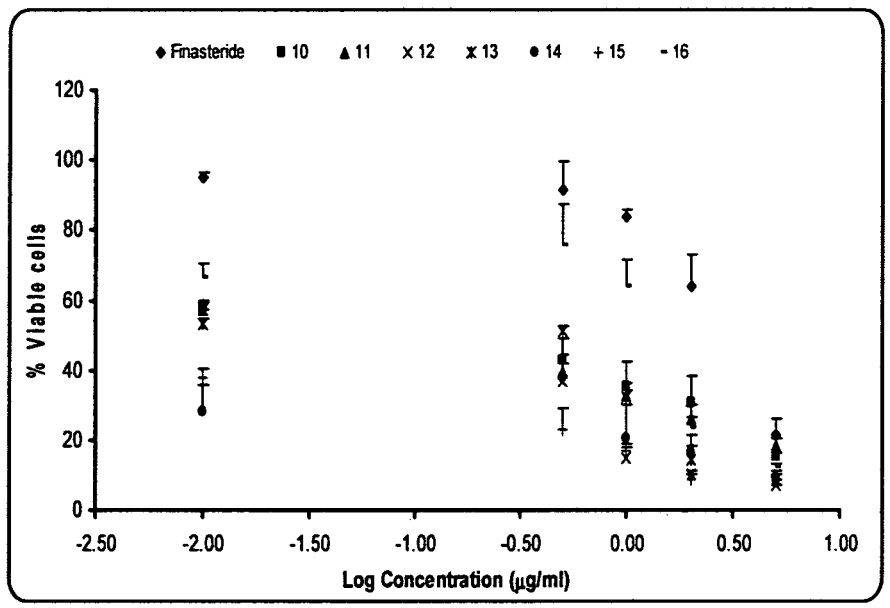
FIG. 5 Log dose-response relationship with regard to cytotoxicity of the compounds on the number of living cells (DU-145) relative to the control. Each point represent a mean±SEM of 3 independent experiments. Linear regressed line was drawn to calculate the IC$_{50}$. ANOVA followed by Tukey's was applied. Data significantly different from the reference drug (p<0.001).

Results:

All the newly synthesized compounds were tested for antiproliferative activity using DU-145 cell line. The results are expressed in terms of percentage growth inhibition (Table 1) and percentage viable cells (FIG. 5).

Esters of 17-oximino-5-androsten3β-ol (10-16), synthesized in our lab revealed a great reduction in the level of cellular cytotoxicity as compared to Finasteride (3). Examination of data of these analogues 10 to 16 demonstrated a great tolerance of phenyl ring and its para-substituted analogues. Unsubstituted analogue 13 and para-substituted (electron donating group) compounds 12, 14 and 15 were found to be the most active compounds with >90% growth inhibition at concentration of 5.0 µg/ml relative to Finasteride (78% at 5.0 µg/ml) (Table 1). On the other hand analogues 10, 11 with electron withdrawing substituent decreased the growth of DU-145 cancer cell lines from 81-84% (relatively less), but still better than Finasteride (78%). Parent Compound 9 has not shown any significant inhibitory effect on cell proliferation.

TABLE 1

Antiproliferative activity of Finasteride and Compounds 9 to 16

| Compound | % growth inhibition (mean ± SEM)[a] | | | | |
|---|---|---|---|---|---|
| | 0.01 µg/ml | 0.5 µg/ml | 1.0 µg/ml | 2.0 µg/ml | 5.0 µg/ml |
| Finasteride | 5.00 ± 1.58 | 8.83 ± 8.40 | 16.48 ± 2.49 | 36.0 ± 8.95 | 78.51 ± 4.63 |
| Parent Compound 9 | $N_i^a$ | $N_i^a$ | $N_i^a$ | $N_i^a$ | $N_i^a$ |
| (10) | 43.41 ± 0.77 | 57.1 ± 5.96 | 64.90 ± 7.40 | 69.17 ± 7.48 | 84.47 ± 0.74 |
| (11) | 41.50 ± 0.71 | 60.51 ± 4.90 | 67.26 ± 3.70 | 74.03 ± 0.77 | 81.53 ± 1.79 |
| (12) | 42.60 ± 2.21 | 62.99 ± 4.78 | 84.99 ± 3.99 | 89.55 ± 0.96 | 92.94 ± 0.13 |
| (13) | 47.02 ± 1.67 | 48.86 ± 1.66 | 67.62 ± 1.62 | 85.87 ± 4.08 | 91.10 ± 2.10 |
| (14) | 71.82 ± 4.24 | 62.10 ± 11.39 | 79.54 ± 7.76 | 83.89 ± 6.70 | 91.02 ± 1.25 |
| (15) | 62.65 ± 2.46 | 76.89 ± 5.94 | 83.08 ± 0.75 | 91.39 ± 1.50 | 91.54 ± 0.19 |
| (16) | 33.59 ± 7.66 | 24.25 ± 6.37 | 36.19 ± 9.85 | 76.52 ± 5.58 | 87.81 ± 1.11 |

$N_i^a$ = no significant growth inhibition

Number of ester derivatives bearing oxime group (NOH) at C-17, connected directly to the steroidal D ring were synthesized and screened in vitro (Table 1 and FIG. 5). Examination of data of these analogues 10 to 16 demonstrated a great tolerance of phenyl ring and its para-substituted analogues. This is in agreement with the previous reports that have pointed out the importance of aromatic and p-substituted aromatic esters. Unsubstituted analogue 13 and compounds 12, 14 and 15 with an electron donating moiety at para position have been found to be more potent than the reference Finasteride. Compounds 12, 14 and 15 were found to be the most active with >90% growth inhibition at concentration of 5.0 µg/ml relative to Finasteride (78% at 5.0 µg/ml). On the other hand analogues 10, 11 with electron withdrawing substituents demonstrated relatively less activity than above compounds but still better than Finasteride. Parent Compound 9 has not shown significant antiproliferative activity.

b) In Vivo (Effect on Steroid Androgen Level)

Treatment of Animals

Animals (Sprague Dawley male rats weighing 150-200 g) were divided into 3 groups; vehicle (control), Finasteride (standard), treated (test sample) and each group consist of 5 animals. Sprague Dawley rats were treated intraperitoneally with Finasteride 40 mg/kg and equimolar dose of compounds. After 6 hr of treatment, blood was withdrawn by cardiac puncture under diethyl ether anesthesia and serum was separated from cells by centrifugation. Plasma testosterone values were obtained by ELISA plate reader at 550 nm and are given in ng/ml.

Elisa

The aliquots of 50 µl of each of standards, control and unknown (serum samples) were added to Testosterone Antibody coated wells. 100 µl of HRP-testosterone conjugate was added to all the wells and the plates were shaken gently on a shaker for proper mixing of the reagents. Following 4 hr of incubation at 37° C., the incubation mixture was removed. The wells were washed with phosphate buffer for 5-6 times (200 µl each time), followed by addition of 100 µl of TMB/ $H_2O_2$ substrate in each of the wells. The plates were further incubated at 37° C. for 20 minutes. At the end of incubation reaction was stopped by using 100 µl of 0.5 M $H_2SO_4$ as stopping reagent. The absorbance of each well was read on Elisa plate reader at 450 nm [Rassaie, M. J.; Kumari, G. L.; Pandey, P. K.; Gupta, N.; Kochupillai, N.; Grover, P. K. *Steroids* 1992, 57, 288 and Hosoda, H.; Yoshida, H.; Sakai, Y.; Miyairi, S.; Nambara, T. *Chem. Pharm. Bull.* 1980, 28, 3035]

Results

Figure 6:
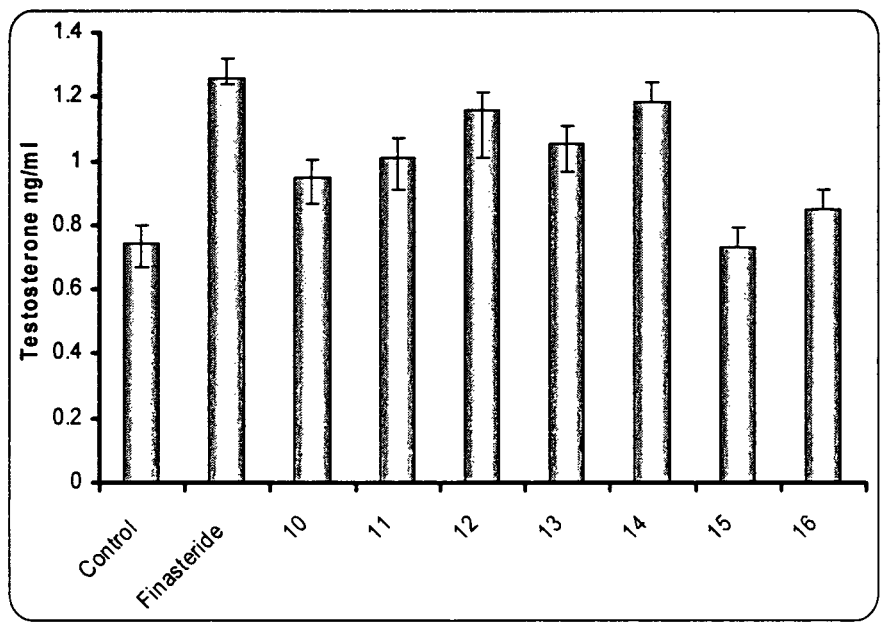
FIG. 6 Effect of compounds on serum level of testosterone. Results are mean±SEM of five experiments. *p<0.05 significant as compared to control, $^{a}$p<0.05 significant as compared to Finasteride.

The effect of compounds (10 to 16) and Finasteride on the serum concentration of testosterone are reported in Table 2 and FIG. 6.

Serum 'T' level were increased in Finasteride treated rats (1.26±0.02 ng/ml compared with 0.742±0.07 ng/ml control rats). It is apparent from Table 2 and FIG. 6 that almost all the ester derivatives of 17-oximino-5-androsten-3β-ol were able to increase the serum testosterone level as compared to control except compound 15. The 6 hr post dose serum T levels were 1.05±0.08 ng/ml for the compound 13 with unsubstituted phenyl group. Ester derivatives 12 and 14 with electron releasing group at p-position of phenyl ring has been found to have increased activity, while presence of electron withdrawing moiety at this position causes the loss of activity (10, 11). Significant increase in level of serum testosterone level has been found in the compound 16.

TABLE 2

Serum levels of Testosterone

| | T (ng/ml) | SEM |
|---|---|---|
| Control | 0.742 | 0.07301 |
| Finasteride | 1.26 | 0.02264 |
| 10 | 0.95 | 0.07759 |
| 11 | 1.01 | 0.10149 |
| 12 | 1.16 | 0.14835 |
| 13 | 1.05 | 0.08385 |
| 14 | 1.19 | 0.05975 |
| 15 | 0.73 | 0.02588 |
| 16 | 0.85 | 0.05489 |

Discussion:

Intact male rats (Sprague Dawley, 200-250 g) were used in the designed study in which various compounds were compared for in vivo 5α-reductase inhibitory potency, as judged by the their ability to attenuate the conversion of testosterone into dihydrotestosterone (DHT). ELISA for testosterone were found to be suitable for determination in serum of rate since the cross reactive DHT levels were extra low in male. The procedure measure T equally well, and method met all the requirement of precision, accuracy, sensitivity and selectivity.

c) In Vitro Cytotoxicity Using Mouse Macrophages (Acute Toxicity)

In vitro cytotoxicity test using DU-145 cells in the preliminary evaluation of anticancer drug enable us to select most potent compound, but cytotoxic agents however frequently exhibit-unspecific toxicity. Nevertheless the ability to selectively kill the target cell remains a highly desirable property of potential new therapeutic cytotoxic agents. In this study, we have demonstrated the applicability of Red dye uptake (MTT) assay using mouse macrophages (Balb C) for in vitro toxicity testing of newly synthesized compounds.

Preparation of Test Material

All steroids were dissolved in ethanol and diluted to appropriate concentration: 0.01, 0.5, 1.0, 2.0, 5.0 µg/ml from the two stock solution of 1 mg/ml and 0.001 µg/ml. Stocks were maintained at room temperature.

Cell Viability Assay

Isolation of Mouse Macrophages

Albino mice (laca strain) weighing 20-25 g of either sex were sacrificed by cervical dislocation and small cut was given on peritoneal skin with a help of scissors. Approximately 1 ml of Phosphate buffer saline preincubated at 37° C. was injected into cavity. The abdomen was lavaged for 10 min and fluid along with macrophages were taken out using a syringe into polypropylene tube. The phosphate solution was spun at 800 rpm for 5-10 min and cells were resuspended in 1 ml RPMI media. Cell number was counted using haemocytometer.

$$\text{Final cell count} = \frac{\text{Total cell count} \times 1000 \times \text{dilution factor}}{0.1 \times 5}$$

0.1=chamber depth, 5 Number of squares (each square is 1 mm)

MTT Assay

Cells (mouse macrophages) were plated at a density of $5 \times 10^3$ cells/well in 96 plate at 37° C. in 5% $CO_2$. Cells were exposed in graded concentration of compounds at designated various concentration. Each concentration was tested in triplicate wells. After 48 hr fresh MTT 20 µl (1 mg/ml) was added directly to all the wells and culture was incubated for 4 hr at 37° C. During this incubation, MTT was converted into a water insoluble formazan complex by metabolic activity of viable cells. Formazan crystal were taken and dissolved in 100 µl of DMSO, which give light pink colour. The absorbance of each well was read on Elisa plate reader (Merck) at 570 nm. The spectrometer was calibrated to zero absorbance using culture medium without cells. The relative cell viability (%) related to control well containing cell culture medium without drug was calculated by [A]test/[A]control×100.

% Cell Viability=$[A]_{test}/[A]_{control} \times 100$ $[A]_{test}$=absorbance test sample
$[A]_{control}$=absorbance control sample
Results: $LC_{50}$: Concentration of the Compound in µg/ml (µm), Lethal to 50% Population of Cells.

Red dye uptake (MTT) assay, demonstrated the toxicity of the compounds towards normal cell by using mouse macrophages. The assay quantifies the viable cells, after 24 hr incubation of cells with five different concentrations. Results in Table 3 and FIG. 7 demonstrated a direct and proportional relation between cell number and concentration.

The results obtained from MTT assay were statistically significant (P<0.001) and linear equation obtained allowed us to determine toxicity index ($LC_{50}$) i.e., concentration of the compound in µg/ml (µm), lethal to 50% population of cells. The summarized data is presented in Table 4. Data from this study Table 4 clearly indicated that compounds 13 and 16 with high $LC_{50}$ values were non toxic to mouse macrophages. Whereas acute toxicity of the compounds 10-12, 14 and 15 were comparable to Finasteride.

TABLE 3

% Viable Cells of derivative (10 to 16 )

| Compound | % viable Cells (mean ± SEM)[a] | | | | |
|---|---|---|---|---|---|
| | 0.01 µg/ml | 0.5 µg/ml | 1.0 µg/ml | 2.0 µg/ml | 5.0 µg/ml |
| Finasteride | 96.45 ± 0.36 | 94.20 ± 1.72 | 93.32 ± 0.59 | 81.18 ± 0.20 | 79.14 ± 0.312 |
| (10) | 88.22 ± 0.41 | 87.21 ± 0.46 | 77.40 ± 0.43 | 77.14 ± 0.21 | 73.149 ± 0.13 |
| (11) | 88.79 ± 0.19 | 86.50 ± 0.107 | 76.74 ± 0.107 | 76.30 ± 0.46 | 75.85 ± 0.259 |
| (12) | 79.39 ± 0.77 | 77.46 ± 0.75 | 73.03 ± 0.36 | 69.10 ± 0.84 | 65.26 ± 2.79 |
| (13) | 87.71 ± 0.29 | 84.74 ± 0.27 | 83.61 ± 0.20 | 83.85 ± 0.28 | 82.99 ± 0.36 |
| (14) | 85.75 ± 0.28 | 77.69 ± 0.38 | 76.80 ± 0.23 | 75.82 ± 0.33 | 72.82 ± 0.28 |
| (15) | 89.80 ± 2.95 | 81.02 ± 2.83 | 63.99 ± 0.91 | 56.88 ± 0.39 | 55.36 ± 0.19 |
| (16) | 80.79 ± 2.30 | 78.32 ± 0.89 | 77.04 ± 0.23 | 77.31 ± 0.37 | 77.37 ± 0.16 |

TABLE 4

Acute Toxicity of the compounds

| S. No. | Compound | $LC_{50}$ (µm). |
|---|---|---|
| 1. | Finasteride | 28.2 |
| 2. | 10 | 24.0 |
| 3. | 11 | 19.5 |
| 4. | 12 | 22 |
| 5. | 13 | 89.4 |
| 6. | 14 | 29.4 |
| 7. | 15 | 22.0 |
| 8. | 16 | 89 |

Figure 7:
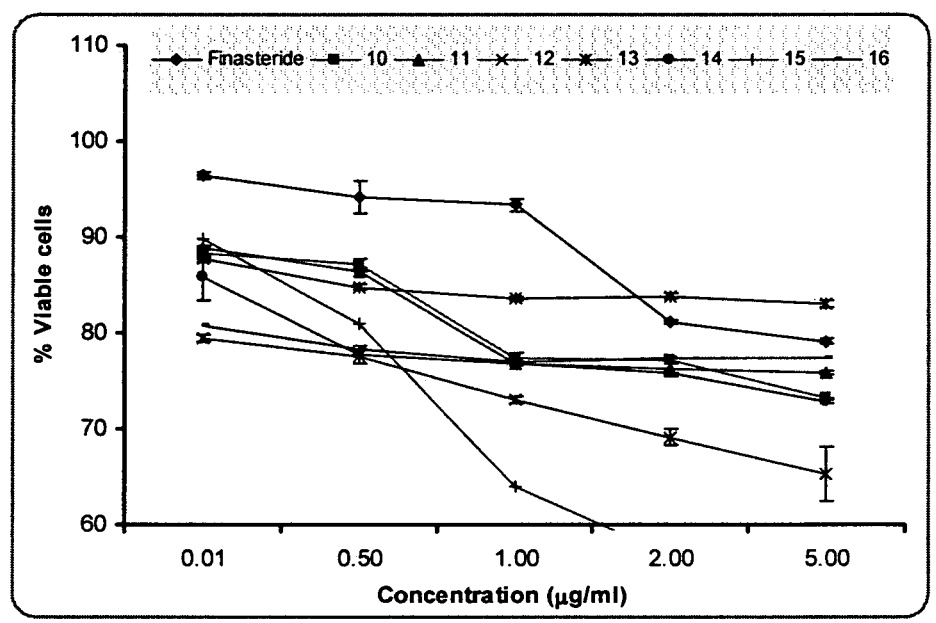
FIG. 7 Toxicity of the compounds to mouse macrophages (Balb C). Cell viability was determined based on the MTT assay. Each point represent a mean value and SEM of 3 independent experiments. *p<0.001 are significantly different compared to Finasteride according to the one-way ANOVA followed by Tukey's test.

In vitro cytotoxicity test using DU-145 cells in the preliminary evaluation of anticancer drug enable us to select most potent compound, but cytotoxic agents however frequently exhibit-unspecific toxicity. Nevertheless the ability to selectively kill the target cell remains a highly desirable property of potential new therapeutic cytotoxic agents. In this study, we have demonstrated the applicability of Red dye uptake (MTT) assay using mouse macrophages (Balb C) for in vitro toxicity testing of newly synthesized compounds. The assay quantifies the viable cells, after 24 hr incubation of cells with five different concentrations. FIG. 7 and Table 3 demonstrated a direct and proportional relation between cell number and concentration.

Data from this study Table 4 clearly indicated that compounds 13 and 16 with high $LC_{50}$ values were non toxic to mouse macrophages. Acute toxicity of the compounds 10-12, 14 and 15 were comparable to finasteride We have synthesized seven new steroidal esters derivative of 17-oximino-5-androsten-3-ol, starting from Dehydroandrosterone acetate. Newly synthesized compounds were tested for their antiproliferative activity and 5α-reductase inhibitory activity in comparison to Finasteride. Decreased androgen level have been found in serum of animal treated with newly synthesized compounds. These compounds have also shown better cytotoxicity in comparison to reference drug Finasteride. Thus such compounds can be useful in treatment of androgen dependent disorder of prostate alone or by synergistic effect they can decrease the size of prostate due to their antiproliferative activity.

We claim:

1. Steroidal esters of 17-oximino-5-androsten-3β-ol of general formula A or pharmaceutically acceptable salts thereof

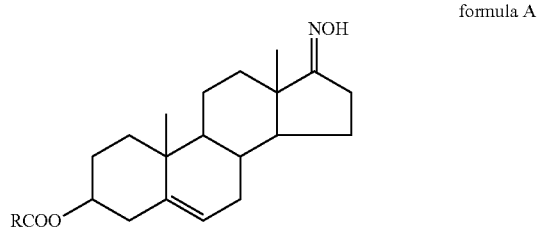

formula A wherein R is selected from a group consisting of, 4-methylbenzyl, and 4-aminobenzyl.

2. The compound according to claim 1 wherein the pharmaceutically acceptable salt is selected from the group consisting of hydrochloride, sulphates, phosphates acetates, propionates; and sodium, potassium and calcium salts of the phenolic hydroxyl groups containing substrates.

3. The compound according to claim 1 wherein the compounds showed antiproliferative activity with a >90% growth inhibition of DU-145 cell at a concentration of 5.0 μm/ml.

4. The compound according to claim 1 wherein the compounds showed increase of serum level of testosterone as compared to control at a dose of 40 mg/kg.

5. The compound according to claim 1 wherein the compounds have LC50 in the range of 22 to 29.4 mm.

6. The compound according to claim 1 wherein the compounds are non-toxic at a concentration ranging between 0.01 μg/ml to 5.0 μg/ml.

7. A process for the preparation of novel steroidal esters of 17-oximino-5-androstene-3β-01 of formula A according to claim 1, wherein the process comprises:
(i) reacting 17-oximino-5-androstene-3β-01 with an organic acid and dicyclohexylcarbodiimide (DCC) in anhydrous dichloromethane for a period ranging between 24-48 hours at a temperature ranging between 20 to 25° C.,
(ii) filtering the precipitated dicyclohexylurea (DCU) and removing the solvent from the filtrate under vacuum and the residue was crystallized to obtain the desired product.

8. A pharmaceutical composition comprising: a therapeutically effective amount of a compound of claim 1 or a pharmaceutically acceptable salt thereof optionally along with a pharmaceutically acceptable carrier, excipient, diluent.

* * * * *